(12) United States Patent
Kawana

(10) Patent No.: US 8,389,289 B2
(45) Date of Patent: Mar. 5, 2013

(54) GAS CHROMATOGRAPHY APPARATUS

(75) Inventor: Shuichi Kawana, Osaka (JP)

(73) Assignee: Shimadzu Corporation, Kyoto-shi (JP)

( * ) Notice: Subject to any disclaimer, the term of this patent is extended or adjusted under 35 U.S.C. 154(b) by 648 days.

(21) Appl. No.: 12/557,187

(22) Filed: Sep. 10, 2009

(65) Prior Publication Data

US 2010/0064770 A1  Mar. 18, 2010

(30) Foreign Application Priority Data

Sep. 12, 2008  (JP) .................. 2008-234265

(51) Int. Cl.
*G01N 30/86* (2006.01)
(52) U.S. Cl. ........ 436/161; 422/89; 73/23.35; 73/23.36; 95/82; 96/101; 96/102; 702/22; 702/24
(58) Field of Classification Search ............ 422/70, 422/89; 73/23.35–23.42, 61.52–61.58; 95/82–89; 96/101–107; 702/22–25
See application file for complete search history.

(56) References Cited

U.S. PATENT DOCUMENTS

2008/0234945 A1* 9/2008 Walk et al. ............... 702/19

FOREIGN PATENT DOCUMENTS

JP   2006-292446 A   10/2006
WO  WO2007/012643   *  2/2007

* cited by examiner

*Primary Examiner* — Jan Ludlow
(74) *Attorney, Agent, or Firm* — Sughrue Mion, PLLC

(57) ABSTRACT

A gas chromatograph (GC) apparatus capable of detecting abnormality, in which a reference retention index is obtained from a result obtained by analyzing a given substance and a retention-index reference substance under adequate analysis conditions using a normal column, and stored in a storage section. Further, under a condition that the apparatus can perform normal analysis, the given substance is subjected to GC analysis to obtain a reference retention time, and the obtained reference retention time is stored in the storage section. A diagnosis processing section is operable to compare each of an actual retention time and an actual retention index with a respective one of the reference retention time and the reference retention index. If a deviation therebetween or abnormality is detected, the diagnosis processing section is operable to estimate a causal factor of the abnormality.

6 Claims, 2 Drawing Sheets

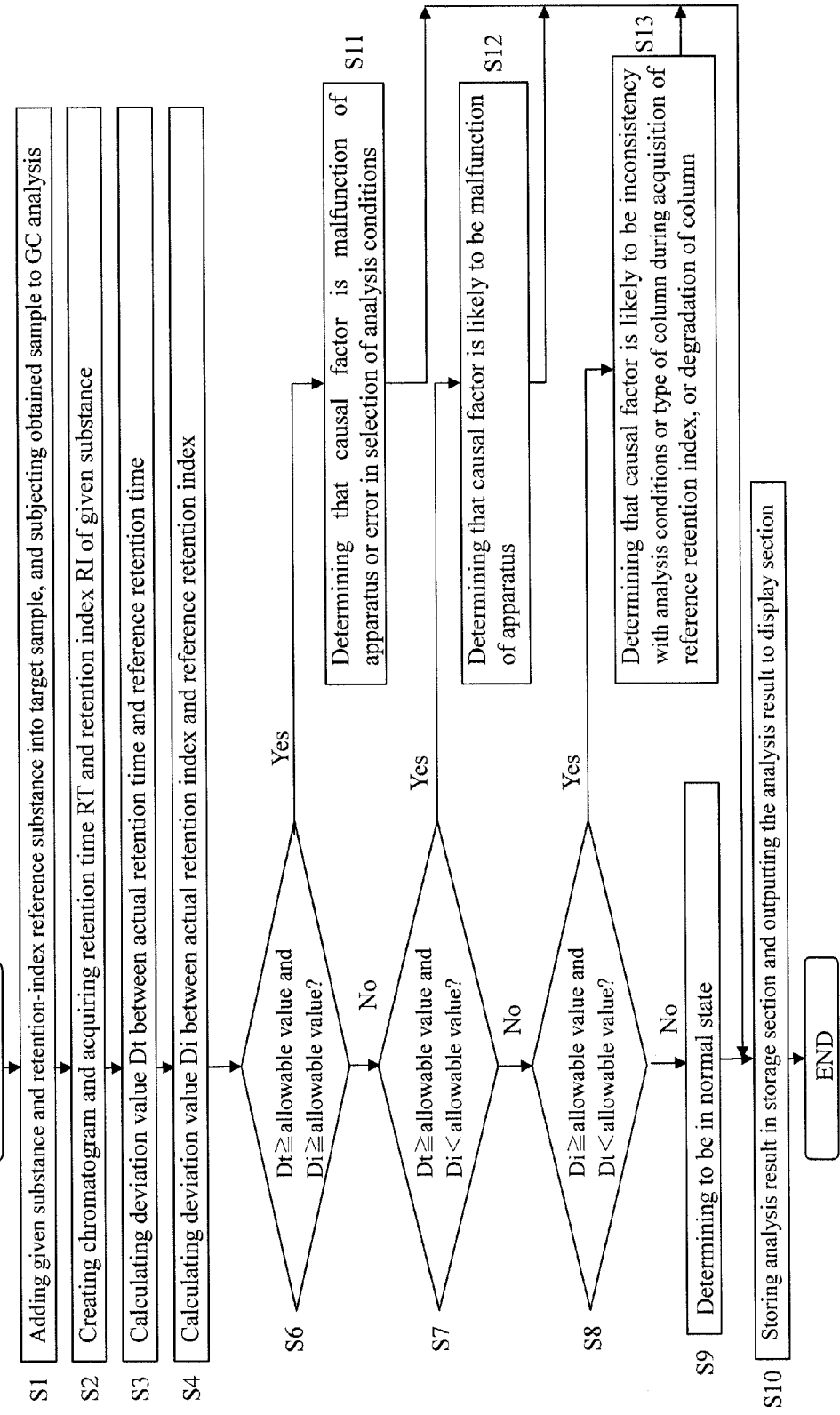

GAS CHROMATOGRAPHY APPARATUS

BACKGROUND OF THE INVENTION

1. Field of the Invention

The present invention relates to a gas chromatograph apparatus for separating components of a sample using a column and analyzing the separated components. The gas chromatograph apparatus of the present invention may be implemented using any type of detector, which means that it includes a gas chromatograph/mass spectrometer (GC/MS).

2. Description of the Background Art

Heretofore, as means for verifying whether gas chromatographic (GC) analysis is normally performed in a gas chromatograph (GC) apparatus, an inspection has been carried out in such a manner that a given compound is subjected to GC analysis using a certain column and under certain analysis conditions to obtain a retention time thereof and register the obtained retention time as a reference retention time, and, at an appropriate subsequent timing, the given compound is subjected to GC analysis using the same column and under the same analysis conditions to obtain an actual retention time thereof and compare the actual retention time with the registered reference retention time. However, in case where there is a difference (deviation) between the actual and reference retention times, an assumed factor causing the difference includes a considerable number of malfunctions of the apparatus and errors in analytical procedure. Thus, although the presence or absence of abnormality in analysis can be evaluated, it is difficult to identify a causal factor of the abnormality.

As means for evaluating a level of degradation in a column as one consumable component, there has been known a technique using a retention index of a given substance with respect to a reference substance (typically, n-alkane), as disclosed in the following Patent Document 1. This technique makes it possible to accurately evaluate the column degradation level, so that a maintenance operation, such as cutoff of an inlet end of a column or replacement of a column, can be performed at an appropriate timing. However, even in inspection based on the retention index, abnormality in the analysis is not always caused by only column degradation but can be caused by another factor.

[Patent Document 1] JP 2006-292446A

SUMMARY OF THE INVENTION

In view of the above problems, it is an primary object of the present invention to provide a gas chromatograph apparatus capable of maximally identifying various defects in gas chromatographic analysis, such as malfunctions of the apparatus, inconsistency in analysis conditions, erroneous installation of a column and degradation in a column itself, and informing a user of the identified defects.

In order to achieve this object, the present invention provides a gas chromatograph apparatus which comprises (a) first storage means which stores, as a reference retention index, a retention index of a given substance with respect to a retention-index reference substance, wherein the retention index of the given substance is obtained by gas chromatographic analysis using a normal column, (b) second storage means which stores, as a reference retention time, a retention time of the given substance obtained by normal gas chromatographic analysis using the gas chromatograph apparatus, (c) actual information acquisition means operable to acquire a current actual retention time and a current actual retention index of the given substance, based on data obtained by subjecting to gas chromatographic analysis a target sample containing the given substance and the retention-index reference substance added thereto, (d) status diagnostics means operable to diagnose a state of the apparatus and adequacy of analysis conditions, based on both a difference between the actual retention index and the reference retention index stored in the first storage means and a difference between the actual retention time and the reference retention time stored in the second storage means, and (e) output means operable to output a result of the diagnosis by the status diagnostics means.

As used herein, the term "normal column" means a column which can be deemed to have a stationary phase (liquid phase) identical or equivalent to that of a column used in the gas chromatograph apparatus. The retention-index reference substance to be used herein is typically n-alkane.

In the gas chromatograph apparatus of the present invention, the status diagnostics means is operable to evaluate a state of the apparatus state and adequacy of analysis conditions, based on a combination of a deviation in retention time of the given substance and a deviation in retention index of the given substance. Specifically, for example, if both the deviation in retention time of the given substance and the deviation in retention index of the given substance are large, a causal factor is assumed to be a malfunction of the apparatus or a complete inconsistency in analysis conditions. If the deviation in retention time of the given substance is large whereas the deviation in retention index of the given substance is small, it would result from a phenomenon that both the given substance and the retention-index reference substance flow out of a column after similar delays, and thus it is assumed that a causal factor is likely to be a malfunction of the apparatus causing, for example, delay in timing of sample injection. If the deviation in retention time of the given substance is small whereas the deviation in retention index of the given substance is large, and given that the apparatus has no malfunction, a causal factor is assumed to be a defect, such as degradation in a column, installation of a column having a stationary phase (liquid phase) unequivalent to that of a column used during acquisition of the reference retention index, or analysis conditions different from those during the acquisition of the reference retention index.

For example, the output means is operable to graphically display the diagnosis result from the state diagnosis means onto a display screen, and indicate one or more of a plurality of defect items, or one or more positions or sections of the apparatus, as a potential causal factor of the abnormality. Based on such information, a user can quickly take measures to avoid further continuation of data acquisition and analysis, under an inadequate situation.

Preferably, in the gas chromatograph apparatus of the present invention, the given substance comprises at least two substances consisting of a first substance susceptible to degradation in a column and a second substance insusceptible to the column degradation, wherein the gas chromatograph apparatus is configured to allow the diagnosis to be performed for each of the at least two substances, based on actual and reference retention times and actual and reference retention indexes of the at least two substances. Specifically, the first substance susceptible to the column degradation is a substance having high adsorbability, such as a nitrogen-containing compound, and the second substance insusceptible to the column degradation is a substance having high stability and low adsorbability, such as carbon hydride.

In the above case, if a deviation in retention index of the first substance susceptible to the column degradation is large, it can be evaluated that a causal factor is more likely to be the column degradation than other defects. If a deviation in retention index of the second substance insusceptible to the column degradation is large, it can be evaluated that a causal factor is likely to be a defect other than the column degradation. In this manner, instead of using only one type of given substance, a plurality of types of given substances each having a different property may be used to effectively utilize actual and reference retention times and actual and reference retention indexes thereof. This makes it possible to enhance credibility of the diagnosis and facilitate identifying a causal factor of abnormality.

In one specific embodiment, the gas chromatograph apparatus of the present invention further comprises third storage means which stores, as a reference peak-area value, a peak-area value calculated from a peak of the given substance appearing on a chromatogram during the gas chromatographic analysis for obtaining the reference retention time, and wherein the actual information acquisition means is operable to acquire a current actual peak-area value of the given substance, and the status diagnostics means is operable to perform the diagnosis by additionally using a difference between the actual peak-area value and the reference peak-area value stored in the third storage means. In this specific embodiment, the actual peak-area value and the reference peak-area value of the given substance obtained under a condition that a concentration and an amount of the given substance are kept constant, are compared with each other. This makes it possible to more clearly identify a malfunction of the apparatus and an inconsistency in a column or analysis conditions with those during acquisition of the reference retention index.

As above, the gas chromatograph apparatus of the present invention can detect an abnormality in gas chromatographic analysis caused by various defects, such as a malfunction of the apparatus, an error in selection of a column, degradation in a column, and an error in selection of analysis conditions, during the gas chromatographic analysis for a target sample, and estimate a causal factor of the abnormality with a high degree of accuracy. In addition, the gas chromatograph apparatus of the present invention can inform a user of the estimated causal factor to allow the user to quickly take measures, such as checkup, correction and/or maintenance of a defect procedure and/or a defective section of the apparatus. Further, this allows the user to avoid the use of data acquired under such a defective situation.

BRIEF DESCRIPTION OF THE DRAWINGS

FIG. 2 is a flowchart showing a process of an apparatus diagnosis in the gas chromatograph apparatus according to the embodiment.

DESCRIPTION OF THE EXEMPLARY EMBODIMENTS

Figure 1:
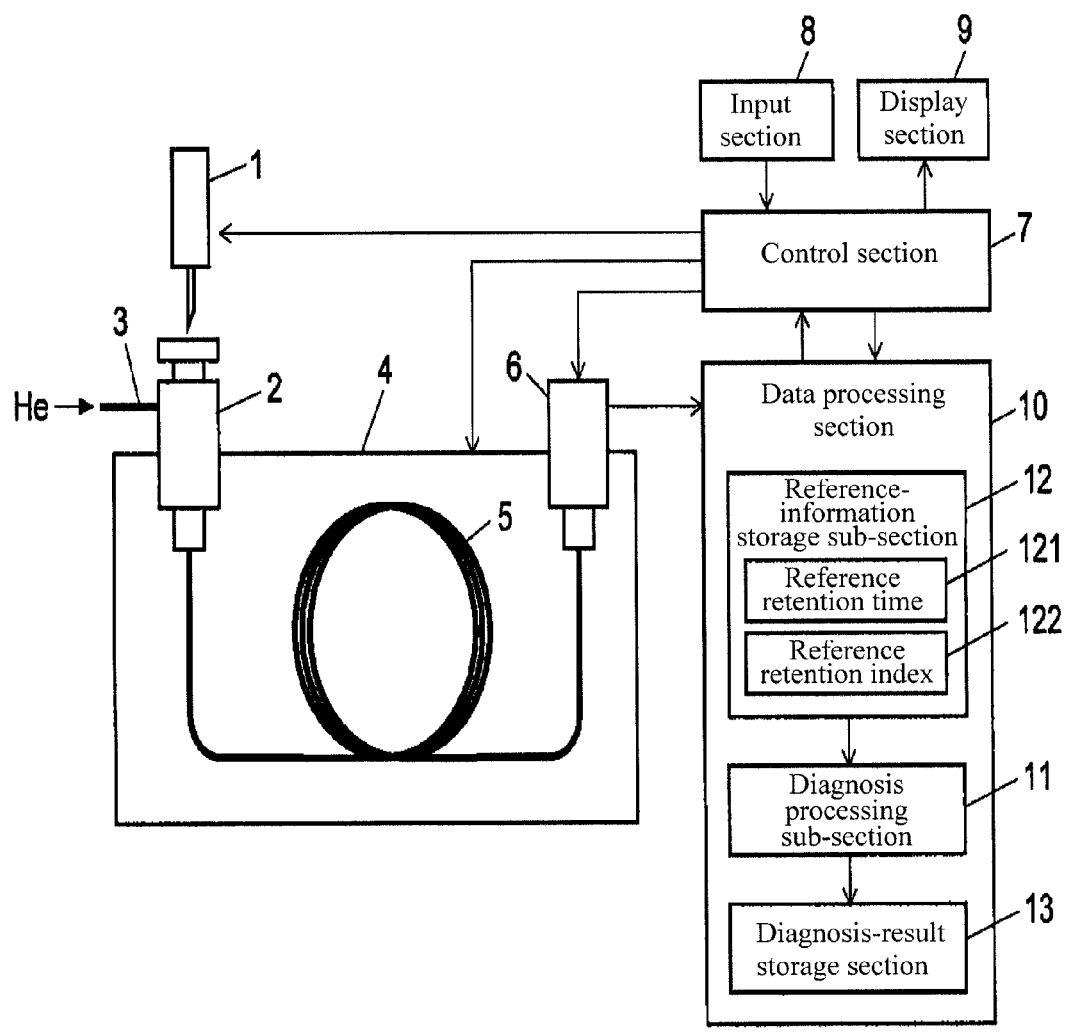
FIG. 1 is a block diagram showing a general configuration of a gas chromatograph apparatus according to one exemplary embodiment of the present invention.

With reference to the accompanying drawings, the present invention will now be described based on one exemplary embodiment thereof. FIG. 1 is a block diagram showing a general configuration of a gas chromatograph (hereinafter referred to as "GC") apparatus according to the embodiment.

A sample-vaporizing chamber 2 is provided at an inlet of a column 5 installed in a column oven 4, and a carrier gas (in this embodiment, helium gas) is sent from a carrier gas feed pipe 3 into the column 5 at a constant flow rate. When a small amount of liquid sample is injected from an injector 1 into the sample-vaporizing chamber 2 at a given timing under control of a control section 7, the injected liquid sample is vaporized within a short time of period, and the vaporized sample is sent into the column 5 on a stream of the carrier gas. Based on the column oven 4, the column 5 is maintained at a constant temperature (for analysis at constant temperature), or controllably heated up according a given heating program (for analysis at elevated temperature). Various compounds contained in the sample are separated from each other during passing of the column 5, and introduced from the column 5 into an outflow detector 6 with different time lags.

The detector 6 is not limited to a specific type, but may be any suitable type, such as a hydrogen flame ionization detector, a flame photometric detector, an electron capture detector, and a thermal conductivity detector, or may be a mass spectrometer. The detector 6 is operable to detect the compounds in the sample gas introduced therein with time, and a detected signal of the detector 6 is sent to a data processing section 10. The data processing section 10 is operable to create a chromatogram based on the detection signal and then subject the created chromatogram to a given waveform processing so as to carry out qualitative analysis and quantitative analysis. The control section 7 is operable to control respective operations of the data processing section 10 and various other sections to achieve a GC analysis operation. The control section 7 is connected with an input section 8 for allowing a user to issue various instructions and set operating conditions therethrough, and a display section 9 for displaying an analysis result. For example, functions of the control section 7 and the data processing section 10 may be mostly achieved by executing a given control/processing program on a personal computer.

In order to perform an after-mentioned distinctive apparatus diagnosis operation, the data processing section 10 comprises a diagnosis processing sub-section 11, a reference-information storage sub-section 12 and a diagnosis-result storage sub-section 13. The reference-information storage sub-section 12 is capable of storing therein a reference retention time 121 and a reference retention index 122.

In the GC apparatus according to this embodiment, the reference retention time 121 and the reference retention index 122 are stored in the reference-information storage sub-section 12 in advance of initiation of apparatus diagnosis. For this purpose, under specified analysis conditions, a given substance and a retention-index reference substance are subjected to GC analysis using a normal column without degradation. In this embodiment, the retention-index reference substance is n-alkane. Although the number of type of the given substance may be one, a plurality of types of given substances may be used, as described later. Through this GC analysis, a retention index of the given substance with respect to n-alkane can be calculated. Then, the obtained retention index is stored in the reference-information storage sub-section 12, as the reference retention index 122. It is understood that the GC analysis for acquiring the reference retention index 122 is not necessarily performed using the GC apparatus used by the user. Further, the reference retention index 122 is not necessarily obtained through GC analysis performed by the user himself/herself, but may be obtained using a retention index database which is available to the public.

Then, through the use of the GC apparatus according to this embodiment, the given substance and n-alkane serving as the retention-index reference substance are subjected to GC analysis in a normal state of the GC apparatus, and a retention time and a retention index of the given material are calculated from a result of this GC analysis. The obtained retention tine is stored in the reference-information storage sub-section 12, as the reference retention time 121. Further, the obtained retention index may be compared with the reference retention index 122 to effectively utilize for inspection on whether functions and configuration of the GC apparatus are in a normal state.

Subsequently, when a target sample is subjected to GC analysis using the GC apparatus according to this embodiment, an apparatus diagnosis operation is performed along with acquisition of GC analysis data, according to the process as shown in FIG. 2.

Specifically, the given substance and n-alkane are added into the target sample, and the obtained sample is subjected to GC analysis (Step S1). The data processing section 10 creates a chromatogram based on a detection signal obtained by the detector 6. The data processing section 10 further subjects the created chromatogram to a waveform processing to obtain a retention time RT of the given substance and a retention time of the retention-index reference substance, and calculates a retention index RI of the given substance based on the obtained retention times (Step S2). The retention index RI and the retention time RT serve as an actual retention index and an actual retention time, respectively.

The diagnosis processing sub-section 11 reads out the reference retention time 121 and the reference retention index 122 from the reference-information storage sub-section 12, and calculates a deviation value Dt between the actual retention time RT and the reference retention time 121 (Step S3), and a deviation value Di between the actual retention index RI and the reference retention index 122 (Step S4). Based on the two deviation values Dt, Di, various defects as causal factors of abnormality are evaluated in the following manner.

Firstly, it is determined whether the deviation value Dt in retention time is equal to or greater than a first allowable value, and the deviation value Di in retention index is also equal to or greater than a second allowable value (Step S6). If the determination in Step S6 is YES, the routine advances to Step S11. In Step S11, it is determined that a causal factor is a malfunction of the apparatus, or a complete inconsistency in analysis conditions, i.e., an error in selection of analysis conditions.

If the determination in Step S6 is NO, it is determined whether the deviation value Dt in retention time is equal to or greater than the first allowable value, and the deviation value Di in retention index is less than the second allowable value (Step S7). If the determination in Step S7 is YES, the routine advances to Step S12. As a causal factor of the phenomenon that no deviation occurs in retention index although a deviation occurs in retention time, the following typical phenomenon can be assumed. The sample is injected into the sample-vaporizing chamber 2 at a later timing than an original or desirable sample injection timing, and thereby both the given substance and the retention-index reference substance pass through the column 5 after similar delays. Thus, in Step S12, it is determined that the causal factor is likely to be a malfunction of the apparatus, mainly a defect in the control section 7 or the injector 1.

If the determination in Step S7 is NO, it is determined whether the deviation value Di in retention index is equal to or greater than the second allowable value, and the deviation value Dt in retention time is less than the first allowable value (Step S8). If the determination in Step S8 is YES, the routine advances to Step S13. In Step S13, it is determined that a causal factor is any one of an inconsistency in analysis conditions with those during the acquisition of the reference retention index, an inconsistency in column type with that during acquisition of the reference retention index, and deterioration in the column 5.

If the determination in Step S8 is NO, it is determined to be in a normal state, because both the deviation value Di in retention index and the deviation value Dt in retention time are less than the second allowable value and the first allowable value, respectively (Step S9). When any one of Steps S9, S11, S12 and S13 is executed, the diagnosis result is stored in the diagnosis-result storage sub-section 13, and, according to need, displayed on a screen of the display section 9 or printed out from a printer (not shown) (Step S10). Preferably, when the diagnosis result is displayed on the screen of the display section 9, a defect item or a defective section of the apparatus is expressly displayed, for example, by blinking a defective position in a configuration of the apparatus graphically displayed on the screen in a simulated manner.

In the above embodiment, it is determined whether each of the deviation value Dt in retention time of the given substance and the deviation value Di in retention index of the given substance is equal to or greater than an allowable value. Alternatively, a type of defect may be more finely evaluated by determining within which of a plurality of ranges each of the deviation values Dt, Di falls. Further, although the number of types of given substances in the above embodiment is one, a plurality of types of given substances may be used, and respective deviation values in retention time and retention index may be evaluated for each of the given substances. In this case, at least two of the given substances are preferably selected such that a first one of the at least two given substance is susceptible to degradation in a column, and a second one of the at least two substance is insusceptible to the column degradation. In this case, each of the first and second substances can be separately used for identifying a respective one of the column deterioration and the apparatus malfunction to facilitate the determination of a causal factor or defect.

Further, the GC apparatus may be configured to perform the diagnosis by additionally using another parameter other than retention time and retention index of the given substance. For example, such a diagnosis operation may be achieved by calculating a peak-area value of a peak of a given substance appearing on a chromatograph during a GC analysis operation for acquiring a reference retention time of the given substance, storing the peak-area value in the reference-information storage sub-section 12, as a reference peak-area value, subsequently calculating a peak-area value of a peak of the given substance during a GC analysis operation for a target sample, and comparing the actual peak-area value with the reference peak-area value. Further, in the case where a plurality of types of given substances are used, the diagnosis operation may be achieved by storing a ratio of respective reference peak-area values of the given substances in the reference-information storage sub-section 12, calculating a ratio of respective actual peak-area values of the given substances during a GC analysis operation for a target sample, and comparing the actual peak-area ratio with the reference peak-area ratio.

A deviation in peak-area value or peak-area ratio becomes larger, for example, when only a part of a desired amount of sample is injected into the sample-vaporizing chamber 2, or when, in an operation of supplying a vaporized sample from the sample-vaporizing chamber 2 to the column at a given split ratio, the split ratio is set at an abnormal value, or when the detector 6 has a malfunction. Thus, a causal factor of malfunction in the apparatus can be more adequately identified by additionally using such a parameter.

Although the present invention has been fully described by way of example with reference to the accompanying drawings, it is to be understood that various changes and modifications may be made therein without departing from the spirit and scope of the invention as set forth in appended claims.

What is claimed is:

1. A gas chromatograph apparatus comprising:
    (a) first storage means which stores, as a reference retention index, a retention index of a given substance with respect to a retention-index reference substance, the retention index of the given substance being obtained by gas chromatographic analysis using a normal column;
    (b) second storage means which stores, as a reference retention time, a retention time of the given substance obtained by normal gas chromatographic analysis using the gas chromatograph apparatus;
    (c) actual information acquisition means operable to acquire a current actual retention time and a current actual retention index of the given substance, based on data obtained by subjecting to gas chromatographic analysis a target sample containing the given substance and the retention-index reference substance added thereto;
    (d) status diagnostics means operable to diagnose a state of the apparatus and adequacy of analysis conditions, based on both a difference between the current actual retention index and the reference retention index stored in the first storage means and a difference between the current actual retention time and the reference retention time stored in the second storage means;
    (e) a diagnosis processing sub-section operable to calculate a time deviation value between the current actual retention time and the reference retention time and an index deviation value between the current actual retention index and the reference retention index,
    wherein a specific causal factor of abnormality in a gas chromatographic analysis is determined based on the time deviation value and the index deviation value; and
    (f) output means operable to output a result of the diagnosis comprising the specific causal factor by the status diagnostics means.

2. The gas chromatograph apparatus as defined in claim 1, wherein the given substance comprises at least two substances consisting of a first substance susceptible to degradation in a column and a second substance insusceptible to the column degradation, and wherein the gas chromatograph apparatus is configured to allow the diagnosis to be performed for each of the at least two substances, based on retention time and retention index.

3. The gas chromatograph apparatus as defined in claim 1, which further comprises third storage means which stores, as a reference peak-area value, a peak-area value calculated from a peak of the given substance appearing on a chromatogram during the gas chromatographic analysis for obtaining the reference retention time, and wherein:
    the actual information acquisition means is operable to acquire a current actual peak-area value of the given substance; and
    the status diagnostics means is operable to perform the diagnosis by additionally using a difference between the actual peak-area value and the reference peak-area value stored in the third storage means.

4. A method of separating components of a target sample by a gas chromatograph apparatus, the method comprising:
    storing, as a reference retention index, a retention index of a given substance with respect to a retention-index reference substance, the retention index of the given substance being obtained by gas chromatographic analysis using a normal column;
    storing, as a reference retention time, a retention time of the given substance obtained by normal gas chromatographic analysis using the gas chromatograph apparatus;
    acquiring a current actual retention time and a current actual retention index of the given substance, based on data obtained by subjecting to gas chromatographic analysis a target sample containing the given substance and the retention-index reference substance added thereto;
    diagnosing a state of the apparatus and adequacy of analysis conditions, based on both difference between the current actual retention index and the reference retention index stored in the first storage means and a difference between the current actual retention time and the reference retention time stored in the second storage means;
    calculating time deviation value between the current actual retention time and the reference retention time and an index deviation value between the current actual retention index and the reference retention index,
    wherein a specific causal factor of abnormality in a gas chromatographic analysis is determined based on the time deviation value and the index deviation value; and
    outputting a result of the diagnosis comprising the determined specific causal factor.

5. The method of claim 4, wherein the given substance comprises at least two substances consisting of a first substance susceptible to degradation in a column and a second substance insusceptible to the column degradation, and wherein the gas chromatograph apparatus is configured to allow the diagnosis to be performed for each of the at least two substances, based on retention time and retention index.

6. The method of claim 4 further comprising:
    storing, as a reference peak-area value, a peak-area value calculated from a peak of the given substance appearing on a chromatogram during the gas chromatographic analysis for obtaining the reference retention time;
    acquiring a current actual peak-area value of the given substance; and
    performing a diagnosis by additionally using a difference between the actual peak-area value and the reference peak-area value stored in the third storage means.

* * * * *